United States Patent
Matsubara

(10) Patent No.: US 10,175,224 B2
(45) Date of Patent: Jan. 8, 2019

(54) METHOD FOR IDENTIFYING TARGET CELL AND TARGET CELL IDENTIFICATION DEVICE

(71) Applicant: FUJIFILM Corporation, Tokyo (JP)

(72) Inventor: Kenta Matsubara, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/935,227

(22) Filed: Mar. 26, 2018

(65) Prior Publication Data

US 2018/0209954 A1 Jul. 26, 2018

Related U.S. Application Data

(63) Continuation of application No. PCT/JP2016/077556, filed on Sep. 16, 2016.

(30) Foreign Application Priority Data

Sep. 29, 2015 (JP) .................................. 2015-191957

(51) Int. Cl.
*G01N 33/49* (2006.01)
*G01N 21/27* (2006.01)
(Continued)

(52) U.S. Cl.
CPC ............. *G01N 33/49* (2013.01); *G01N 21/27* (2013.01); *G01N 21/31* (2013.01); *G01N 21/41* (2013.01); *G01N 21/84* (2013.01); *G01N 33/48* (2013.01)

(58) Field of Classification Search
CPC ........ G01N 33/49; G01N 21/27; G01N 21/31; G01N 21/41; G01N 21/84
(Continued)

(56) References Cited

U.S. PATENT DOCUMENTS

| | | | |
|---|---|---|---|
| 2009/0087074 A1 | 4/2009 | Wong et al. | |
| 2009/0237502 A1* | 9/2009 | Maiya | G02B 21/367 348/79 |
| 2009/0238437 A1 | 9/2009 | Levine et al. | |
| 2013/0130265 A1 | 5/2013 | Parikh et al. | |
| 2015/0219543 A1 | 8/2015 | Yamauchi et al. | |

FOREIGN PATENT DOCUMENTS

| | | |
|---|---|---|
| JP | 2004-248619 A | 9/2004 |
| JP | 2010-540931 A | 12/2010 |

(Continued)

OTHER PUBLICATIONS

Purwosunu et al., "Clinical Potential for Noninvasive Prenatal Diagnosis through Detection of Fetal Cells in Maternal Blood", Taiwanese Journal Obstetrics and Gynecology, Mar. 2006, vol. 45, No. 1, pp. 10-20 (total 11 pages).

(Continued)

*Primary Examiner* — Roy M Punnoose
(74) *Attorney, Agent, or Firm* — Sughrue Mion, PLLC

(57) ABSTRACT

Provided are a robust and high throughput method for identifying a target cell and a target cell identification device. The method for identifying a target cell includes an image acquisition step of irradiating a specimen with a plurality of light rays having different wavelengths and acquiring a plurality of phase difference images of the specimen, a selection step of selecting a plurality of target cell candidates from the specimen based on a difference in absorption coefficients with respect to the plurality of light rays having different wavelengths, a brightness ratio acquisition step of acquiring brightness ratios between a central part and a peripheral part of each target cell candidate based on the plurality of phase difference images, and a sorting step of sorting a target cell and a non-target cell from the plurality of target cell candidates based on the brightness ratios.

10 Claims, 11 Drawing Sheets

(51) Int. Cl.
  *G01N 33/48* (2006.01)
  *G01N 21/41* (2006.01)
  *G01N 21/31* (2006.01)
  *G01N 21/84* (2006.01)

(58) Field of Classification Search
  USPC .......................................................... 356/39
  See application file for complete search history.

(56) References Cited

FOREIGN PATENT DOCUMENTS

| JP | 2013-190406 A | 9/2013 |
|----|---------------|--------|
| JP | 2014-41140 A | 3/2014 |
| JP | 2014-44050 A | 3/2014 |
| JP | 2014-235033 A | 12/2014 |
| JP | 2015-146747 A | 8/2015 |
| WO | 2013/075100 A1 | 5/2013 |
| WO | 2016/021310 A1 | 2/2016 |

OTHER PUBLICATIONS

International Search Report dated Dec. 6, 2016, issued by the International Searching Authority in application No. PCT/JP2016/077556.
Written Opinion dated Dec. 6, 2016, issued by the International Searching Authority in application No. PCT/JP2016/077556.
International Preliminary on Patentability Report dated Apr. 3, 2018, issued by the International Searching Authority in application No. PCT/JP2016/077556.

* cited by examiner

PHASE DIFFERENCE IMAGE ACQUIRED BY IRRADIATION
WITH LIGHT RAY HAVING FIRST WAVELENGTH (420 nm)

PHASE DIFFERENCE IMAGE ACQUIRED BY IRRADIATION
WITH LIGHT RAY HAVING SECOND WAVELENGTH (540 nm)

PHASE DIFFERENCE IMAGE ACQUIRED BY IRRADIATION
WITH LIGHT RAY HAVING FIRST WAVELENGTH (420 nm)

PHASE DIFFERENCE IMAGE ACQUIRED BY IRRADIATION
WITH LIGHT RAY HAVING SECOND WAVELENGTH (540 nm)

PHASE DIFFERENCE IMAGE ACQUIRED
WITH LIGHT HAVING WAVELENGTH OF 420 nm

PHASE DIFFERENCE IMAGE ACQUIRED
WITH LIGHT HAVING WAVELENGTH OF 480 nm

PHASE DIFFERENCE IMAGE ACQUIRED
WITH LIGHT HAVING WAVELENGTH OF 540 nm

PHASE DIFFERENCE IMAGE ACQUIRED
WITH LIGHT HAVING WAVELENGTH OF 650 nm

PHASE DIFFERENCE IMAGE ACQUIRED
WITH LIGHT HAVING WAVELENGTH OF 420 nm

PHASE DIFFERENCE IMAGE ACQUIRED
WITH LIGHT HAVING WAVELENGTH OF 480 nm

PHASE DIFFERENCE IMAGE ACQUIRED
WITH LIGHT HAVING WAVELENGTH OF 540 nm

PHASE DIFFERENCE IMAGE ACQUIRED
WITH LIGHT HAVING WAVELENGTH OF 650 nm

METHOD FOR IDENTIFYING TARGET CELL AND TARGET CELL IDENTIFICATION DEVICE

CROSS-REFERENCE TO RELATED APPLICATIONS

The present application is a Continuation of PCT International Application No. PCT/JP2016/077556 filed on Sep. 16, 2016 claiming priority under 35 U.S.C § 119(a) to Japanese Patent Application No. 2015-191957 filed on Sep. 29, 2015. Each of the above applications is hereby expressly incorporated by reference, in their entirety, into the present application.

BACKGROUND OF THE INVENTION

1. Field of the Invention

The present invention relates to a method for identifying a target cell and target cell identification device.

2. Description of the Related Art

As prenatal diagnosis, an investigation is underway on identifying a fetus-derived nucleated red blood cell from maternal blood and analyzing, for example, chromosomal deoxyribonucleic acid (DNA) using the nucleated red blood cell.

However, only about one fetus-derived nucleated red blood cell is present in several milliliters (1 mL=$10^{-6}$ m$^3$) of the maternal blood. Therefore, it is important to efficiently identify the fetus-derived nucleated red blood cell (target cell) from the maternal blood (specimen).

JP2010-540931A discloses, as a technique for identifying an object from a specimen, a technique of acquiring images of objects in the specimen, identifying objects of interest in the images, acquiring additional images of the identified objects of interest at a plurality of different wavelengths, and classifying the specimen according to a probabilistic model based on extracted cellular features.

SUMMARY OF THE INVENTION

However, the technique described in JP2010-540931A does not teach a method for identifying cells in a robust and high throughput manner in a case where the specimen is not stained.

The present invention was made in view of the above circumstances, and an object of the present invention is to provide a method for identifying a target cell and a target cell identification device by which a target cell can be robustly identified with high throughput without staining a specimen.

According to an aspect of the present invention, a method for identifying a target cell comprises an image acquisition step of irradiating a specimen with a plurality of light rays having different wavelengths and acquiring a plurality of phase difference images of the specimen, a selection step of selecting a plurality of target cell candidates from the specimen based on a difference in absorption coefficients with respect to the plurality of light rays having different wavelengths, a brightness ratio acquisition step of acquiring brightness ratios between a central part and a peripheral part of each target cell candidate based on the plurality of phase difference images, and a sorting step of sorting a target cell and a non-target cell from the plurality of target cell candidates based on the brightness ratios.

It is preferable that the absorption coefficient is an absorption coefficient of cytoplasm.

It is preferable that the absorption coefficient of cytoplasm is an absorption coefficient of hemoglobin.

It is preferable that the wavelength of one light ray among the plurality of light rays having different wavelengths is 300 nm to 700 nm.

It is preferable that information regarding thicknesses of the target cell and the non-target cell is obtained from the brightness ratios in the sorting step.

It is preferable that the specimen is maternal blood, the target cell candidate is a red blood cell, the target cell is a nucleated red blood cell, and the non-target cell is a non-nucleated red blood cell.

It is preferable that the brightness ratio acquisition step further includes irradiating the plurality of target cell candidates with a light ray having a wavelength different from the different wavelengths of the plurality of light rays in the image acquisition step to acquire an additional phase difference image and acquiring a brightness ratio between a central part and a peripheral part of each target cell candidate based on the additional phase difference image.

It is preferable that a wavelength interval between adjacent light rays in the plurality of light rays having different wavelengths is 72 nm to 540 nm.

According to another aspect of the present invention, a target cell identification device comprises a light source unit which emits a plurality of light rays having different wavelengths to a specimen, an imaging unit which acquires a plurality of phase difference images of the specimen with respect to the plurality of light rays having different wavelengths, and a control unit which identifies a target cell from the specimen based on the plurality of phase difference images, in which the control unit selects a plurality of target cell candidates from the specimen based on a difference in absorption coefficients with respect to the plurality of light rays having different wavelengths, acquires brightness ratios between a central part and a peripheral part of each target cell candidate based on the plurality of phase difference images, and sorts a target cell and a non-target cell from the plurality of target cell candidates based on the brightness ratios.

It is preferable that the control unit controls the imaging unit, acquires an additional phase difference image by irradiating the plurality of target cell candidates with a light ray having a wavelength different from the different wavelengths of the plurality of light rays, and acquires a brightness ratio between a central part and a peripheral part of each target cell candidate based on the additional phase difference image.

According to the present invention, a target cell can be robustly identified with high throughput without staining the specimen.

DESCRIPTION OF THE PREFERRED EMBODIMENTS

Figure 1:
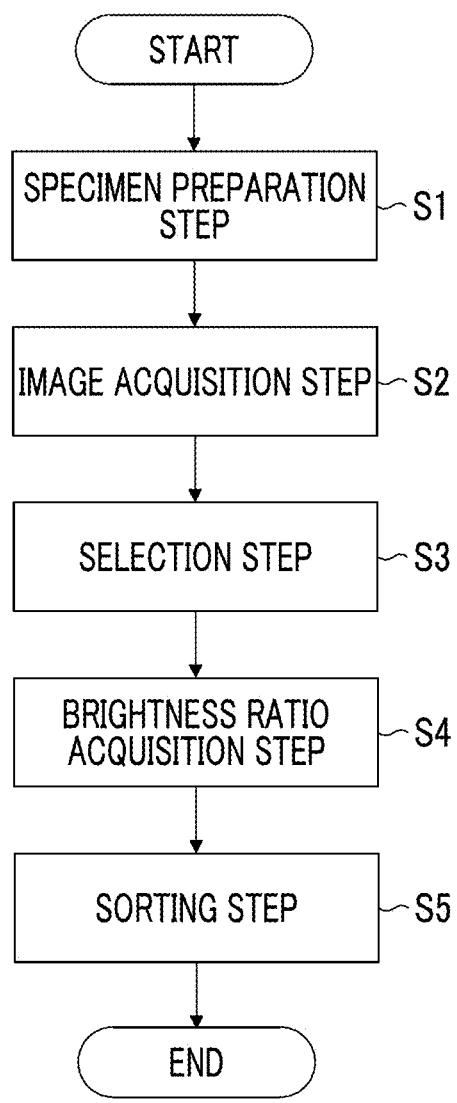
FIG. 1 is a flow chart showing the steps of a method for identifying a target cell.

Hereinafter, a preferred embodiment of the present invention will be described with reference to the accompanying drawings. The present invention will be described by the following preferred embodiment. Modifications can be made by many methods without departing from the scope of the present invention, and embodiments other than the present embodiment can be used. Accordingly, all of the modifications within the scope of the present invention are included in the claims.

Here, in the drawings, the parts represented by the same references are the same elements having the same functions. In addition, in a case where a numerical range is expressed using "to" in the present specification, the numerical values of the upper limit and the lower limit indicated using "to" are also included in the numerical range.

<Method for Identifying Target Cell>

The method for identifying a target cell of the present embodiment will be described by exemplifying a case where a specimen is maternal blood, a target cell candidate is a red blood cell, a target cell is a nucleated red blood cell, and a non-target cell is a non-nucleated red blood cell.

FIG. 1 is a flow chart showing the steps of the method for identifying a target cell of the present embodiment. The method for identifying a target cell of the present embodiment includes a specimen preparation step (Step S1), an image acquisition step (Step S2), a selection step (Step S3), a brightness ratio acquisition step (Step S4), and a sorting step (Step S5). In the specimen preparation step (Step S1), a specimen including target cells which become the objects and non-target cells is collected from a human body, and the specimen is prepared as a sample for identifying the target cells. In the image acquisition step (Step S2), the specimen is irradiated with a plurality of light rays having different wavelengths, and a plurality of phase difference images of the specimen are acquired. In the selection step (Step S3), a plurality of target cell candidates are selected from the specimen based on a difference in absorption coefficients with respect to the plurality of light rays having different wavelengths. In the brightness ratio acquisition step (Step S4), brightness ratios between a central part and a peripheral part of each target cell candidate are acquired based on the plurality of phase difference images. In the sorting step (Step S5), target cells and non-target cells are sorted from the plurality of target cell candidates based on the brightness ratios. Hereinafter, each of the steps will be described.

<Specimen Preparation Step (Step S1)>

In the specimen preparation step, the specimen including the target cells which become the objects and the non-target cells is collected from a human body, and the specimen is prepared as a sample for identifying the target cells. Examples of a method for preparing the specimen as the sample include smearing the specimen on a slide glass, storing the specimen in a Petri dish, storing the specimen in a multi-well plate, and the like. The specimen prepared as the sample is not provided on a prescribed reference plane. Therefore, the minute parts of the target included in the specimen are present at any positions in the specimen without being restricted to a specific position.

Next, description will be made by exemplifying a case of smearing maternal blood on a slide glass.

First, maternal blood is collected from a pregnant mother's body. Peripheral blood of a pregnant mother's body, which has low invasiveness, is preferable as the maternal blood. The peripheral blood of the mother's body includes red blood cells, which are target cell candidates, and maternally derived white blood cells such as eosinophils, neutrophils, basophils, monocytes, lymphocytes, and the like. Furthermore, the red blood cells which are the target cell candidates include nucleated red blood cells (including maternally derived nucleated red blood cells and fetus-derived nucleated red blood cells) which are the target cells and red blood cells that do not include a nucleus which are the non-target cells.

It is known that the fetus-derived nucleated red blood cells are present in the maternal blood from approximately 6 weeks after the start of pregnancy. In a case where the method for identifying a target cell of the present embodiment is applied in prenatal diagnosis, it is preferable that peripheral blood (maternal blood) collected from the mother's body approximately 6 weeks after the start of pregnancy is prepared as the sample.

The fetus-derived nucleated red blood cells are red blood cell precursors that are present in the blood of the mother's body by passing through the placenta. During the mother's pregnancy, the red blood cells of the fetus can be nucleated. In these red blood cells, chromosomes are present, and therefore, the fetus-derived chromosomes and the fetal gene can be obtained by means with low invasiveness. It is known that fetus-derived nucleated red blood cells exist at a ratio of approximately one in $10^6$ cells in the maternal blood, and the existence probability thereof in the maternal blood is extremely low.

The nucleated red blood cells in the maternal blood collected in the collection step is preferably concentrated. As a method for the concentration, a known method such as a density-gradient centrifugation method, a magnetic activated cell sorting (MACS) method, a fluorescence activated cell sorting (FACS) method, a lectin method, or a filtration method using a filter can be used. Among these, concentration is preferably performed by a density-gradient centrifugation method, as a simple concentration method of using the characteristics of blood cells.

Next, a fraction of the maternal blood in which the nucleated red blood cells are concentrated is smeared on a slide glass. As a method for smearing, a glass pulling method (wedge method), a crush method (squash method), a hand spreading method, a spinning method, or the like can be performed, and the glass pulling method is particularly preferably performed. The maternal blood can be smeared on the slide glass by a centrifugal smear method using a chamber slide.

Figure 2:
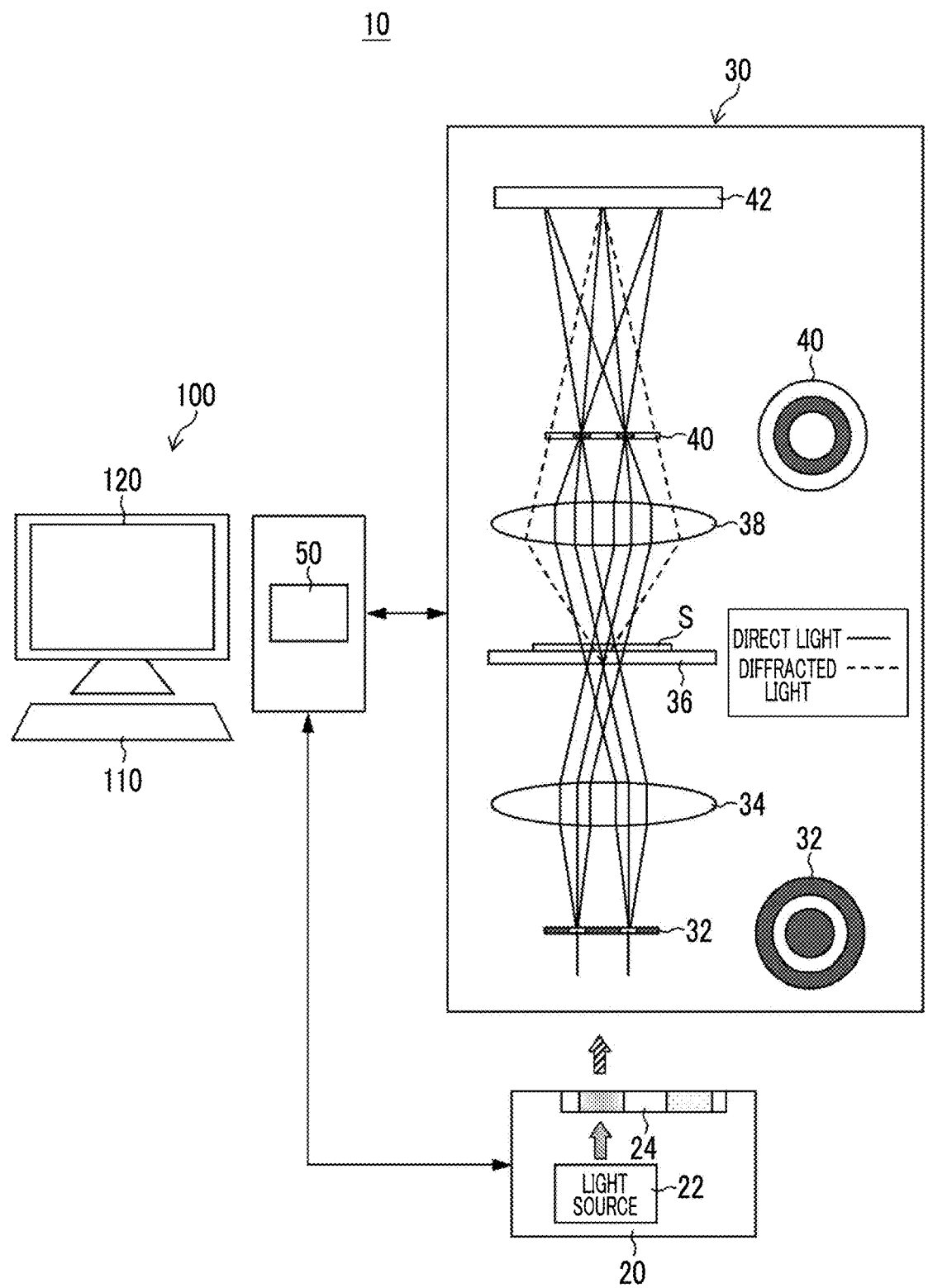
FIG. 2 is a configuration diagram showing the configuration of a target cell identification device.

The specimen thus prepared is provided in a target cell identification device 10, shown in FIG. 2 as a sample S, in a state where the specimen is not subjected to a staining treatment. Since the specimen is not subjected to a staining treatment, damages on the target cell caused by a stain are suppressed. Accordingly, the identified target cell can be accurately analyzed.

The target cell identification device 10 includes a light source unit 20, an imaging unit 30, and a personal computer 100 having a control unit 50. The personal computer 100 is electrically connected to the light source unit 20 and the imaging unit 30. The personal computer 100 having the control unit 50 controls all operations of the target cell identification device 10. The personal computer 100 includes a keyboard 110 serving as an instruction input part and a display 120 serving as a display part.

The light source unit 20 includes a light source 22 and a filter 24. The light source unit 20 can emit the plurality of light rays having different wavelengths to the sample S by causing light from the light source 22 to be transmitted through the filter 24 and switching the wavelength of the light. Examples of the filter 24 include an interference filter and the like. As another aspect, the plurality of light rays having different wavelengths can be emitted to the sample S by preparing a plurality of light source having different wavelengths and switching the light sources.

As the light source 22, for example, a light emitting diode (LED) or light amplification by stimulated emission of radiation (LASER) can be used. The term "different wavelengths" means that the peak wavelengths are different. That is, a wavelength of light is specified by the peak wavelength.

A representative example of the imaging unit 30 is a phase contrast microscope. The imaging unit 30 includes a ring stop 32, a condenser lens 34, a table 36, an objective lens 38, a phase plate 40, and an imaging device 42, from the light source unit 20 side. The sample S is supported by the table 36. The ring stop 32 has an aperture, and light from the light source unit 20 converges, for example, in a ring slit shape by the ring stop 32. The phase plate 40 includes a phase film having the same shape as that of the aperture of the ring stop 32. A phase of light is advanced or retarded by passing through the phase film of the phase plate 40.

The imaging device 42 is installed at a position where an image is formed, and images a phase difference image. The imaging device 42 is not particularly limited, and for example, a charge-coupled device (CCD) camera or a complementary metal oxide semiconductor (CMOS) camera can be used.

Figure 3:
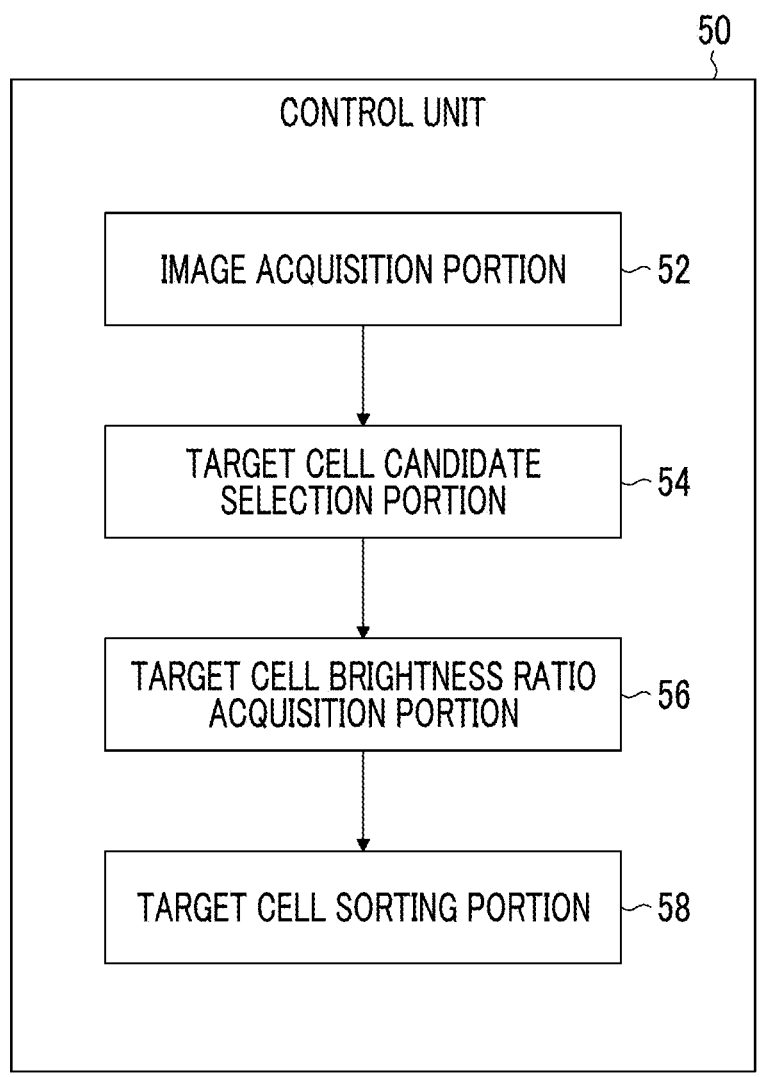
FIG. 3 is a block diagram of a control unit.

FIG. 3 is a block diagram of the control unit 50. As shown in FIG. 3, the control unit 50 includes an image acquisition portion 52, a target cell candidate selection portion 54, a target cell brightness ratio acquisition portion 56, and a target cell sorting portion 58.

The image acquisition step (Step S2), the selection step (Step S3), the brightness ratio acquisition step (Step S4), and the sorting step (Step S5) are executed by using the target cell identification device 10.

<Image Acquisition Step (Step S2)>

In the image acquisition step, the specimen is irradiated with the plurality of light rays having different wavelengths, and the plurality of phase difference images of the specimen are acquired.

Specifically, first, the sample S using the maternal blood as the specimen is placed on the table 36. Next, the light source unit 20 selects a combination of the light source 22 and one filter 24 by a control signal from the image acquisition portion 52 of the control unit 50, that is, a light ray having one wavelength (a light ray having a first wavelength) is selected from the plurality of light rays having different wavelengths. The light source unit 20 radiates the light ray having the first wavelength on the sample S (specimen).

By passing through the ring stop 32, the light ray having the first wavelength converges into light having a ring shape. The light ray having the first wavelength that passes through the ring stop 32 is focused by passing through the condenser lens 34, and the sample S (specimen) is irradiated with this light ray. The light ray having the first wavelength with which the sample S is irradiated passes through the objective lens 38 and the phase plate 40, and forms an image on the imaging device 42.

The light ray having the first wavelength that passes through the sample S is divided into direct light transmitted through the sample S (specimen) and diffracted light diffracted by the sample S (specimen). The direct light that is transmitted through the objective lens 38 passes through the phase film of the phase plate 40, and forms an image on the imaging device 42. Meanwhile, the diffracted light that is transmitted through the objective lens 38 is transmitted through a portion of the phase plate 40, which outside the region where the phase film is formed, and forms an image on the imaging device 42. In a case where the direct light passes through the phase film of the phase plate 40, the phase is shifted in an advancing direction by a ¼ wavelength, or in a retarding direction by a ¼ wavelength.

Since the direct light and the diffracted light having the first wavelength interfere with each other, the image formed on the imaging surface is a phase difference image having a contrast of light and darkness. This image having a contrast of light and darkness is imaged by the imaging device 42, and a phase difference image (first phase difference image) of the specimen at the first wavelength is acquired. The first phase difference image thus acquired is displayed on the display 120 of the personal computer 100 and is stored in a storage device not shown in the drawings.

Next, the light source unit 20 selects a combination of the light source 22 and another filter 24 by a control signal from the control unit 50, that is, a light ray having a wavelength (a light ray having a second wavelength) that is different from the first wavelength is selected from the plurality of light rays having different wavelengths. The light source unit 20 radiates the light ray having the second wavelength on the sample S (specimen).

By passing through the ring stop 32, the light ray having the second wavelength converges into light having a ring shape. The light ray having the second wavelength that passes through the ring stop 32 is focused by passing through the condenser lens 34, and the sample S (specimen) is irradiated with this light ray. The light ray having the second wavelength with which the sample S is irradiated passes through the objective lens 38 and the phase plate 40, and forms an image on the imaging device 42.

Since direct light and diffracted light of the second wavelength interfere with each other, the image formed on the imaging surface is a phase difference image having a contrast of light and darkness. This image having a contrast of light and darkness is imaged by the imaging device 42, and a phase difference image (second phase difference image) of the specimen at the second wavelength is acquired. The second phase difference image thus acquired is displayed on the display 120 of the personal computer 100 and is stored in a storage device not shown in the drawings.

Figure 4A:
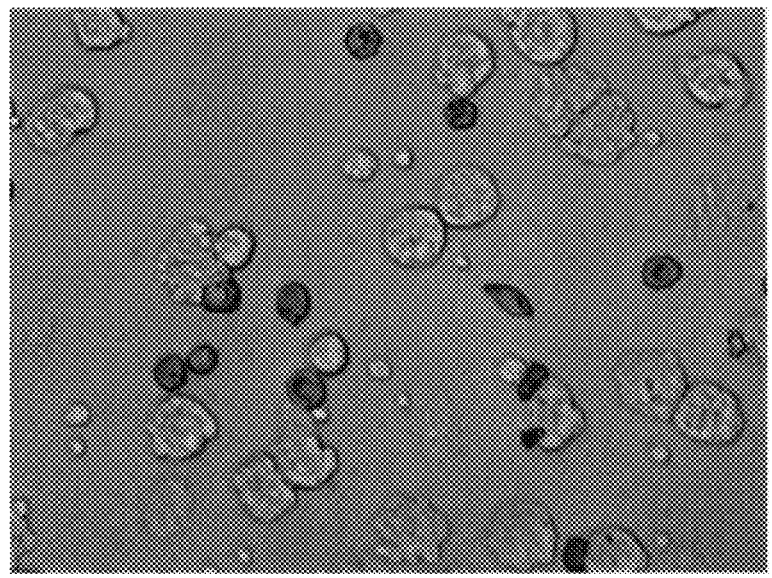
FIGS. 4A and 4B are a plurality of phase difference images acquired by irradiating a sample with a plurality of light rays having different wavelengths.
Figure 4B:
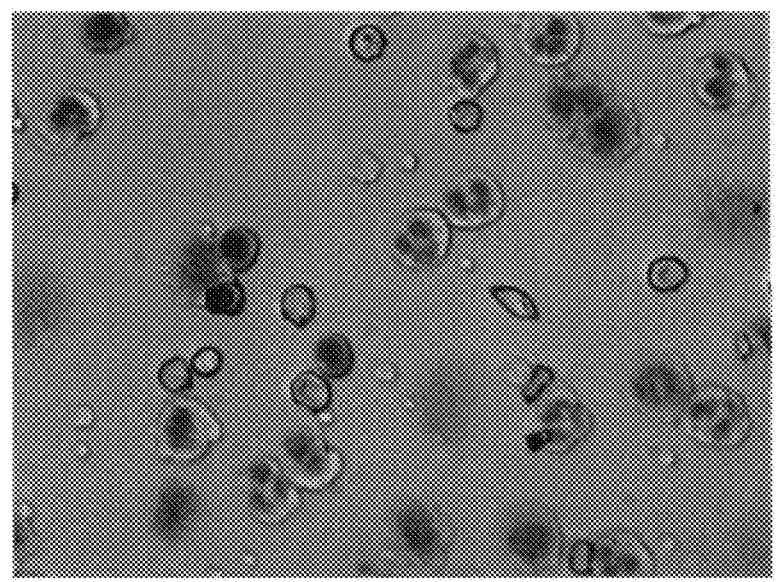

FIGS. 4A and 4B are a plurality of phase difference images acquired by irradiating a sample with a plurality of light rays having different wavelengths. FIG. 4A is the first phase difference image acquired by irradiating the sample S with light having the wavelength of 420 nm as the first wavelength. FIG. 4B is the second phase difference image acquired by irradiating the sample S with light having a wavelength of 540 nm as the second wavelength. In the present embodiment, a case where the first phase difference image and the second phase difference image are acquired as the plurality of phase difference images has been described. The invention is not limited to this embodiment, and it is possible to acquire two or more phase difference images.

<Selection Step (Step S3)>

In the selection step, a plurality of target cell candidates are selected from the specimen based on a difference in absorption coefficients with respect to the plurality of light rays having different wavelengths.

Figure 5:
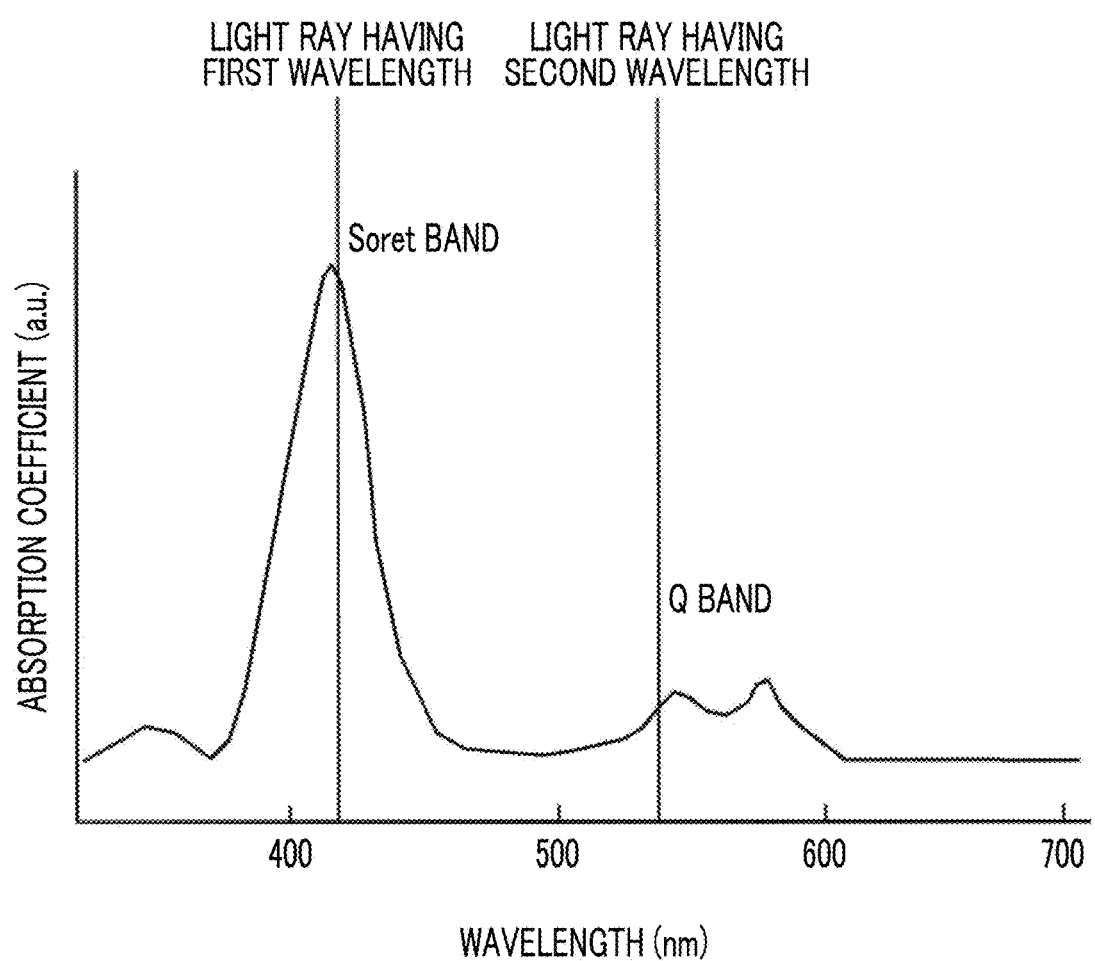
FIG. 5 is a graph showing an absorption coefficient of hemoglobin with respect to a wavelength.

FIG. 5 is a graph showing an absorption coefficient of hemoglobin constituting the cytoplasm of red blood cells with respect to a wavelength. On the graph, the absorption coefficient (a.u.) is indicated on the vertical axis, and the wavelength (nm) is indicated on the horizontal axis. Red blood cells include hemoglobin which is not found in white blood cells. Hemoglobin is an iron-porphyrin complex, and is a complex which has absorption called a Soret band near the wavelength region of 380 nm to 450 nm, deriving from a porphyrin ring, and has absorption called a Q band near the wavelength region of 500 nm to 600 nm.

In the image acquisition step (Step S2), the sample S is irradiated with light having a wavelength of 420 nm as the light ray having the first wavelength, and the sample S is irradiated with light having a wavelength of 540 nm as the light ray having the second wavelength. As shown in FIG. 5, the absorption coefficient of hemoglobin with respect to the light ray having the first wavelength and the light ray having the second wavelength are different. The absorption coefficient of hemoglobin with respect to the light ray having the first wavelength is greater than the absorption coefficient of hemoglobin with respect to the light ray having the second wavelength. In other words, the light ray having the first wavelength is absorbed more by hemoglobin than the light ray having the second wavelength.

According to FIG. 5, at least one light ray among the plurality of light rays having different wavelengths (the light ray having the first wavelength) is preferably a light ray having a wavelength of 300 nm to 700 nm. On the other hand, a light ray having another wavelength among the plurality of light rays having different wavelengths (the light ray having the second wavelength) is preferably a light ray having a wavelength for which the absorption coefficient is different from that for the light ray having the first wavelength. The wavelength of the light ray having another wavelength (the light ray having the second wavelength) is not limited to 300 nm to 700 nm, as long as it is a light ray having a wavelength for which the absorption coefficient is different from that for the light ray having the first wavelength.

Next, the target cell candidate selection portion 54 of the control unit 50 selects red blood cells, which are the plurality of target cell candidates, according to the following procedure.

The red blood cells which are the target cell candidates are distinguished from blood cells other than red blood cells based on the difference in absorption coefficients with respect to the plurality of light rays having different wavelengths (the difference in the absorption coefficients of hemoglobin with respect to the light ray having the first wavelength and the light ray having the second wavelength).

As described above, the absorption coefficients of hemoglobin with respect to the light ray having the first wavelength and the light ray having the second wavelength are different from each other. Accordingly, a brightness ratio between light generated from a red blood cell in a case of irradiation with the light ray having the first wavelength and light generated from the red blood cell in a case of irradiation with the light ray having the second wavelength is large. On the other hand, since the blood cells other than red blood cells (for example, white blood cells) do not include hemoglobin, a brightness ratio between light rays generated from a blood cell other than red blood cells with respect to the plurality of light rays having different wavelengths is small. Since the brightness ratio of the red blood cell with respect to the plurality of light rays having different wavelengths is greater than the brightness ratios of the other blood cells, the red blood cells and blood cells other than red blood cells can be easily distinguished among cells.

The present step is preferably performed in the following aspect.

The target cell candidate selection portion 54 of the control unit 50 acquires brightness ratios between the peripheral part (cytoplasm) in a cell and a non-cell region from the phase difference images with respect to the plurality of light rays having different wavelengths, that is, the first phase difference image and the second phase difference image. In the non-cell region such as a medium, a difference in absorption coefficients with respect to the plurality of light rays having different wavelengths is not large. Therefore, a difference in light rays generated from the non-cell region with respect to the plurality of light rays having different wavelengths (the light ray having the first wavelength and the light ray having the second wavelength) is small. Background components occurring due to the non-cell region such as a medium can be removed or reduced from the phase difference image by acquiring the brightness ratio, which is preferable, since cells (red blood cells and blood cells other than red blood cells) in the sample S (specimen) can be identified.

Figure 6A:
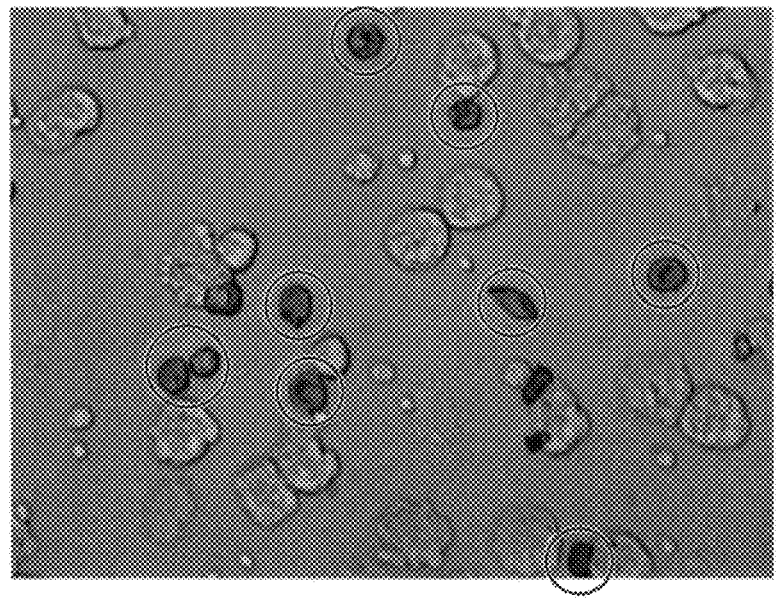
FIGS. 6A and 6B are images specifying red blood cells from the plurality of phase difference images.
Figure 6B:
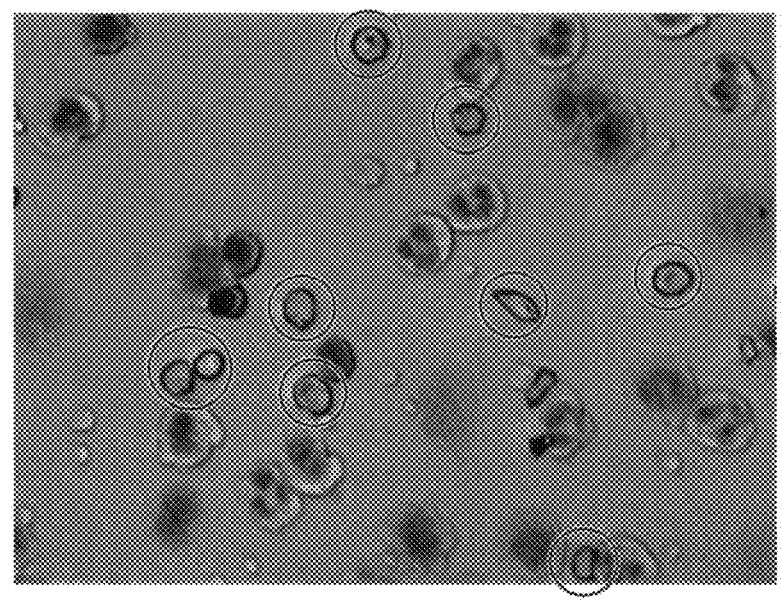

FIGS. 6A and 6B are images specifying red blood cells from the plurality of phase difference images acquired in the image acquisition step (Step S2). The cells surrounded by circles are red blood cells. As shown in FIG. 6A, in a case where the sample S is irradiated with light having a wavelength of 420 nm as the light ray having the first wavelength, the light ray having the first wavelength is absorbed by hemoglobin constituting the cytoplasm of the red blood cells. As a result, light generated from the red blood cells is observed to be black. On the other hand, in a case where the sample S is irradiated with light having a wavelength of 540 nm as the light ray having the second wavelength, the light ray having the second wavelength is barely absorbed by hemoglobin constituting the cytoplasm of the red blood cells. As a result, light generated from the red blood cells is observed to be white. Therefore, the red blood cells can be distinguished from other blood cells in the sample S (specimen).

As described above, in the selection step (Step S3), since the target cell candidates are robustly detected based on the difference in the absorption coefficients of hemoglobin by acquiring the brightness ratios between the peripheral part (cytoplasm) in the cell and the non-cell region, the target cell candidates are easily selected.

<Brightness Ratio Acquisition Step (Step S4)>

In the brightness ratio acquisition step, brightness ratios between the central part and the peripheral part of each target cell candidate are acquired based on the plurality of phase difference images.

In general, the phase contrast microscope constituting the imaging unit 30 acquires a phase difference image having a contrast of light and darkness by superimposing direct light and diffracted light generated by cells in a specimen. The light and darkness of the phase difference image depends on the thickness of the cell (optical path difference) or the wavelength, because the light and darkness is determined by a phase difference between the direct light and the diffracted light.

For this reason, whether a phase is advanced or retarded cannot be determined from the phase difference image. As a result, whether the cell to be identified has a convex shape or has a concave shape cannot be determined. Accordingly, whether the cell has a convex shape or a concave shape (even in a case where there is a difference in the thickness), the same region is observed to be "dark" as the phase difference image.

In a case where the target cell candidates are red blood cells, it is necessary that nucleated red blood cells, which are the target cells, and non-nucleated red blood cell, which are the non-target cells are sorted from the target cell candidates. The nucleated red blood cell and the non-nucleated red blood cell have different thicknesses. However, the difference in the thickness is not distinguished from a conventional phase difference image, as described above.

In the present embodiment, information which allows the target cell and the non-target cell to be distinguished from each other is acquired by acquiring brightness ratios between the central part and the peripheral part of each target cell candidate based on the plurality of phase difference images, as will be described in the sorting step (Step S5). The information which allows the distinguishing is information regarding the shapes of the target cells and the non-target cells and is also information regarding the thicknesses of the target cell and the non-target cell. The information regarding the thicknesses is useful in a case of distinguishing the nucleated red blood cell and the non-nucleated red blood cell.

Figure 7A:
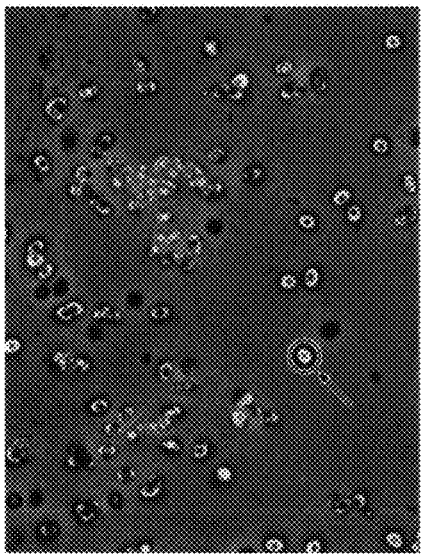
FIGS. 7A to 7D are phase difference images of nucleated red blood cells imaged with a plurality of light rays having different wavelengths.
Figure 7C:
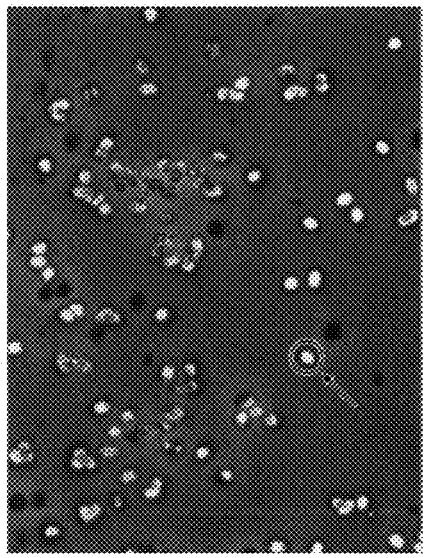
Figure 7B:
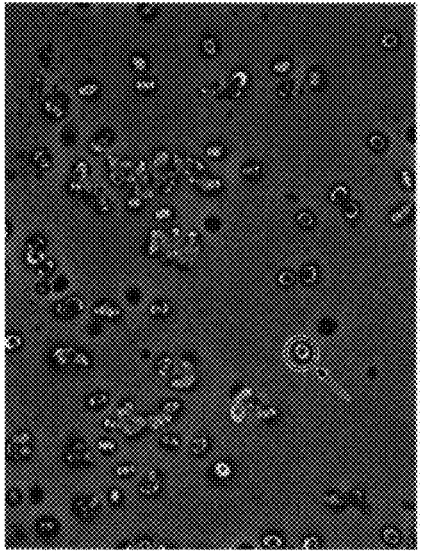
Figure 7D:
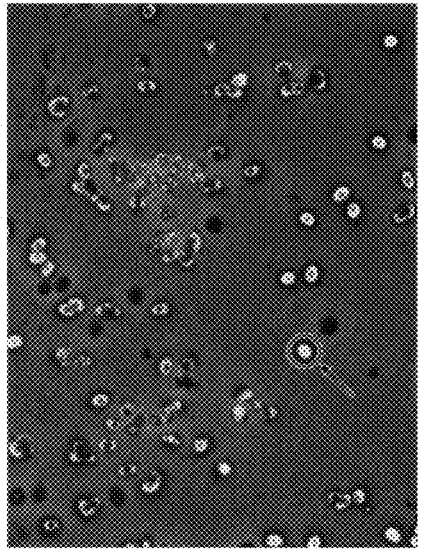

FIGS. 7A to 7D are phase difference images of nucleated red blood cells imaged with a plurality of light rays having different wavelengths. FIG. 7A is a phase difference image of chicken red blood cells imaged with light having a wavelength of 420 nm, FIG. 7B is a phase difference image of the chicken red blood cells imaged with light having a wavelength of 540 nm, FIG. 7C is a phase difference image of the chicken red blood cells imaged with light having a wavelength of 480 nm, and FIG. 7D is a phase difference image of the chicken red blood cells imaged with light having a wavelength of 650 nm. Chicken red blood cells have nuclei.

Figure 8A:
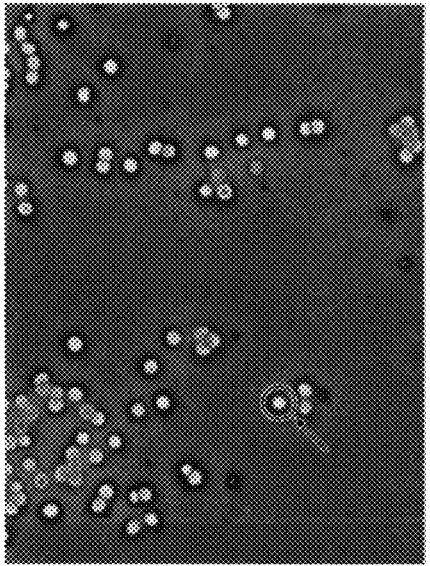
FIGS. 8A to 8D are phase difference images of non-nucleated red blood cells imaged with the plurality of light rays having different wavelengths.
Figure 8C:
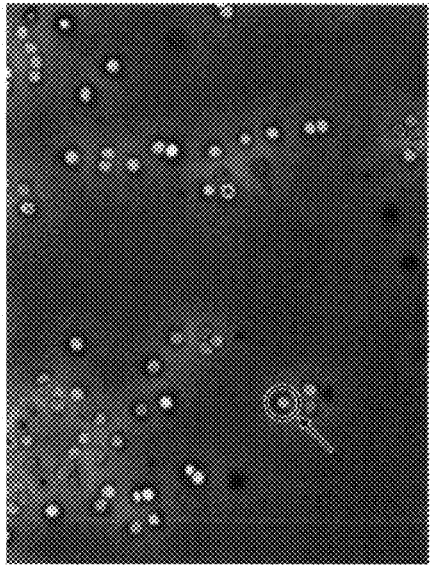
Figure 8B:
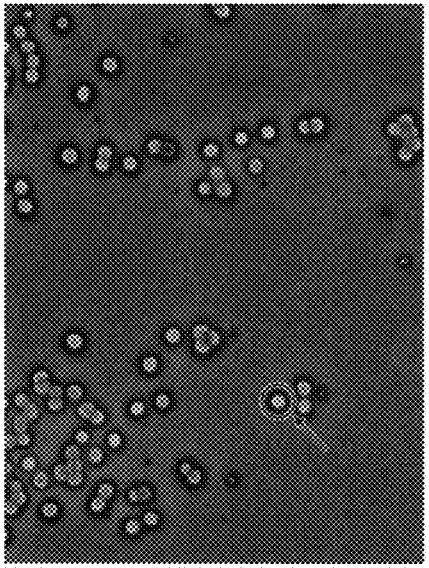
Figure 8D:
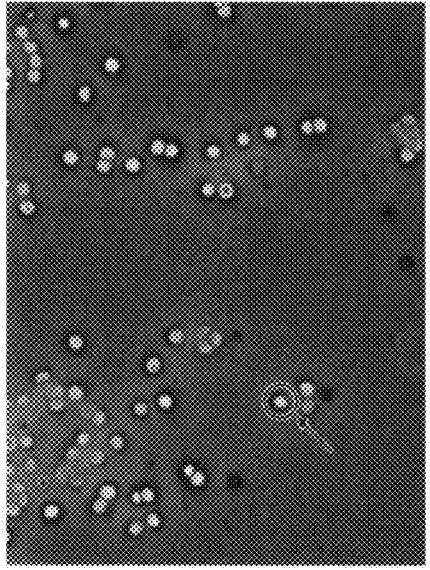

FIGS. 8A to 8D are phase difference images of non-nucleated red blood cells imaged with the plurality of light rays having different wavelengths. FIG. 8A is a phase difference image of human red blood cells imaged with light having a wavelength of 420 nm, FIG. 8B is a phase difference image of the human red blood cells imaged with light having a wavelength of 540 nm, FIG. 8C is a phase difference image of the human red blood cells imaged with light having a wavelength of 480 nm, and FIG. 8D is a phase difference image of the human red blood cells imaged with light having a wavelength of 650 nm. Human red blood cells are denucleated red blood cells.

In FIGS. 7A to 7D, the plurality of target cell candidates (chicken red blood cells) are irradiated with light rays having wavelengths (480 nm and 650 nm) different from the different wavelengths of the plurality of light rays (420 nm and 540 nm) which were radiated in the image acquisition step (Step S2), so as to acquire additional phase difference images (FIG. 7C and FIG. 7D). In FIGS. 8A to 8D, the plurality of target cell candidates (human red blood cells) are irradiated with light rays having wavelengths (480 nm and 650 nm) different from the different wavelengths of the plurality of light rays (420 nm and 540 nm) which were radiated in the image acquisition step (Step S2), so as to acquire additional phase difference images (FIG. 8C and FIG. 8D).

Specifically, the control unit 50 controls the imaging unit 30 and causes the plurality of target cell candidates to be irradiated with light rays having wavelengths different from the different wavelengths of the plurality of light rays which were radiated in the image acquisition step (Step S2), so as to acquire additional phase difference images.

In the brightness ratio acquisition step, information which allows the target cell and the non-target cell to be distinguished from each other can be more accurately acquired by acquiring the additional phase difference images.

Specifically, the target cell brightness ratio acquisition portion 56 of the control unit 50 acquires the brightness ratios between the central part and the peripheral part of each target cell candidate, which is a red blood cell, based on the plurality of phase difference images (including additional phase difference images as necessary).

Figure 9:
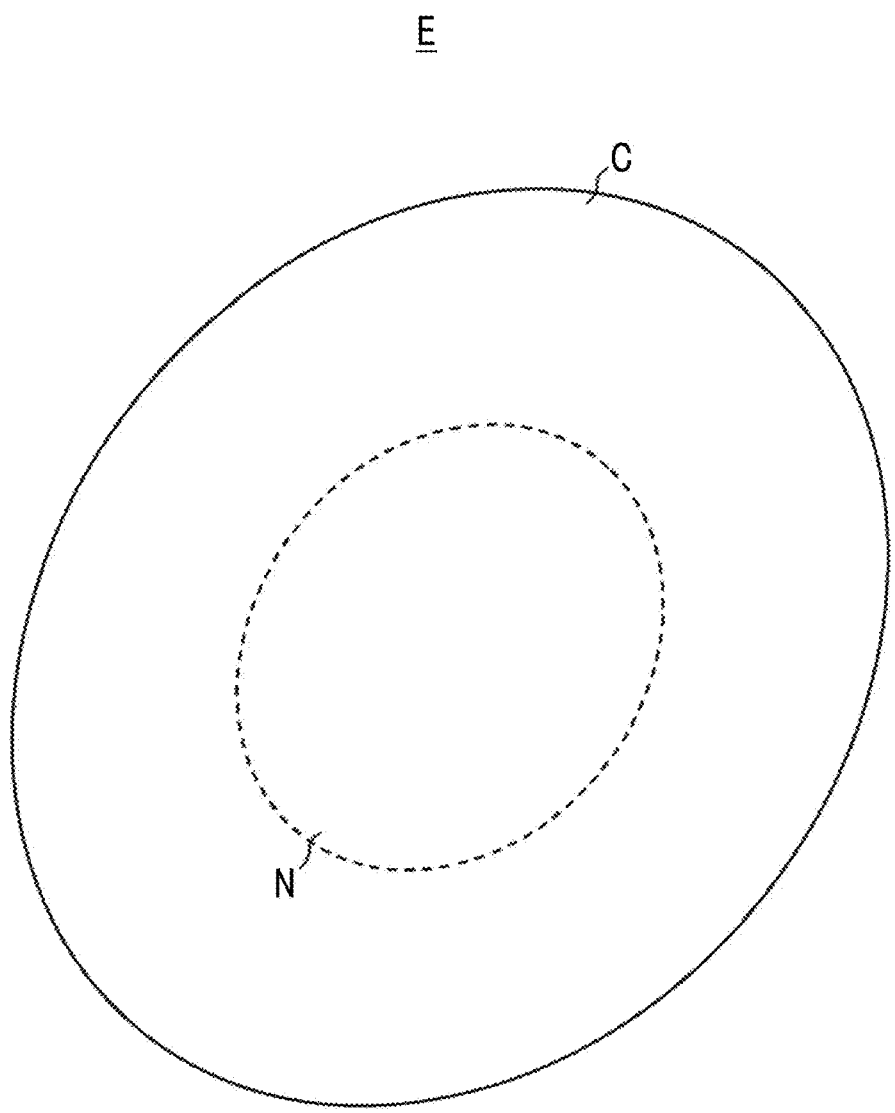
FIG. 9 is a schematic diagram showing a shape of a cell which is a target cell candidate.

FIG. 9 is a schematic diagram showing a red blood cell E which is a target cell candidate. Here, a central part N indicates a region in the cell where a nucleus can exist, and a peripheral part C indicates a region of cytoplasm in the cell, where a nucleus does not exist.

A brightness ratio means a ratio of a brightness of the central part N with respect to a brightness of the peripheral part C of the red blood cell E which is the target cell candidate and can be calculated by the expression (brightness of central part N/brightness of peripheral part C).

In the brightness ratio acquisition step (Step S4), specifically, the brightness ratio between the central part (nucleus) of the cell which is the target cell candidate and the peripheral part (cytoplasm) region in the cell is acquired.

<Sorting Step (Step S5)>

In the sorting step, the target cells and the non-target cells are sorted from the plurality of target cell candidates based on the brightness ratios.

As described in the brightness ratio acquisition step (Step S4), brightness ratios are acquired, thereby acquiring the brightness ratios between the central part and the peripheral part of each target cell candidate based on the plurality of phase difference images. In this way, information which allows the target cell and the non-target cell to be distinguished from each other and information regarding a thickness of a nucleated red blood cell (information reflecting an optical path difference) can be acquired.

Figure 10A:
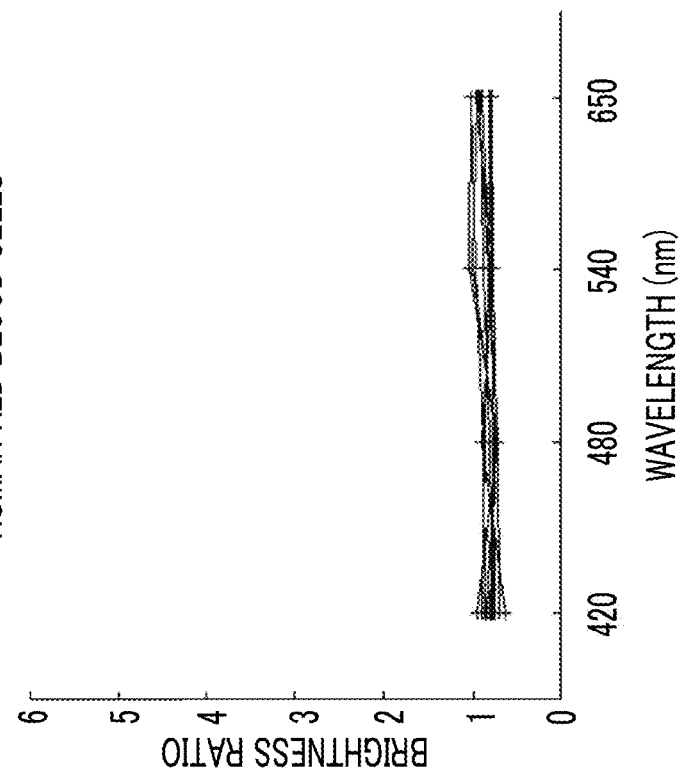
FIGS. 10A and 10B are graphs showing a relationship between a brightness ratio between a central part and a peripheral part of the target cell candidate and a wavelength.
Figure 10B:
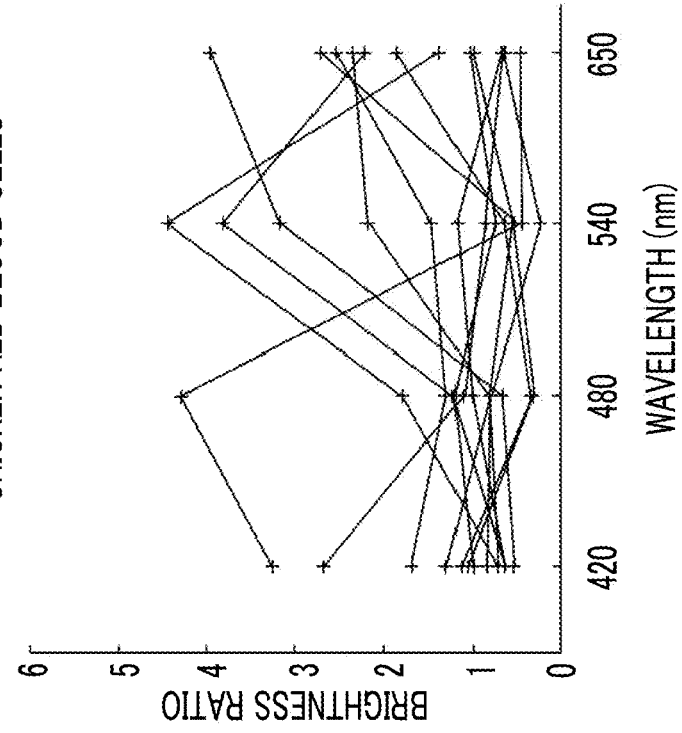

FIGS. 10A and 10B are graphs showing a relationship between a brightness ratio between a central part and a peripheral part of a target cell candidate and a wavelength. The horizontal axis shows the wavelength of light radiated in a case of acquiring a phase difference image, and the vertical axis shows a brightness ratio between a central part and a peripheral part of a target cell candidate in each phase difference image. FIG. 10A shows a relationship between a brightness ratio between a central part and a peripheral part of a chicken red blood cell which is a nucleated red blood cell and a wavelength, and FIG. 10B shows a relationship between a brightness ratio between a central part and a peripheral part of a human red blood cell which is a non-nucleated red blood cell and a wavelength.

In each phase difference image, brightness ratios between the central part and the peripheral part of the target cell candidate located at the same position are calculated. For example, as shown in FIGS. 7A to 7D, brightness ratios of the central part and the peripheral part of the target cell candidate at the position surrounded by a circle are calculated. A brightness ratio for each wavelength is plotted, and each brightness ratio is connected by a straight line. In the present embodiment, a graph shown in FIG. 10A is created by arbitrarily selecting 13 red blood cells, plotting the brightness ratios for each wavelength, and connecting the brightness ratios of the red blood cell located at the same position with a straight line.

For example, as shown in FIGS. 8A to 8D, brightness ratios between the central part and the peripheral part of the target cell candidate at the position surrounded by a circle are calculated, in the same manner described above. A brightness ratio for each wavelength is plotted, and each brightness ratio is connected by a straight line. In the present embodiment, a graph shown in FIG. 10B is created by arbitrarily selecting 8 red blood cells, plotting the brightness ratios for each wavelength, and connecting the brightness ratios of the red blood cell located at the same position with a straight line.

According to the graph of the brightness ratios of the nucleated red blood cell shown in FIG. 10A, it can be recognized that a value of the brightness ratio greatly varies for each wavelength. On the other hand, according to the graph of the brightness ratios of the non-nucleated red blood cell shown in FIG. 10B, it can be recognized that a value of the brightness ratio varies little for each wavelength.

Therefore, by acquiring the brightness ratios between the central part and the peripheral part of each target cell candidate based on the plurality of phase difference images, the information which allows the target cell and the non-target cell to be distinguished from each other and information regarding the thickness of a nucleated red blood cell (information reflecting the optical path difference) can be acquired. As a result, the thickness can be robustly estimated, and information regarding the presence or absence of a nucleus can be acquired by calculating a cycle of variation of the brightness ratios with respect to the wavelength.

Next, description will be made regarding how the variation in the brightness ratios in a nucleated red blood cell reflects the thickness of the nucleated red blood cell (optical path difference).

Figure 11:
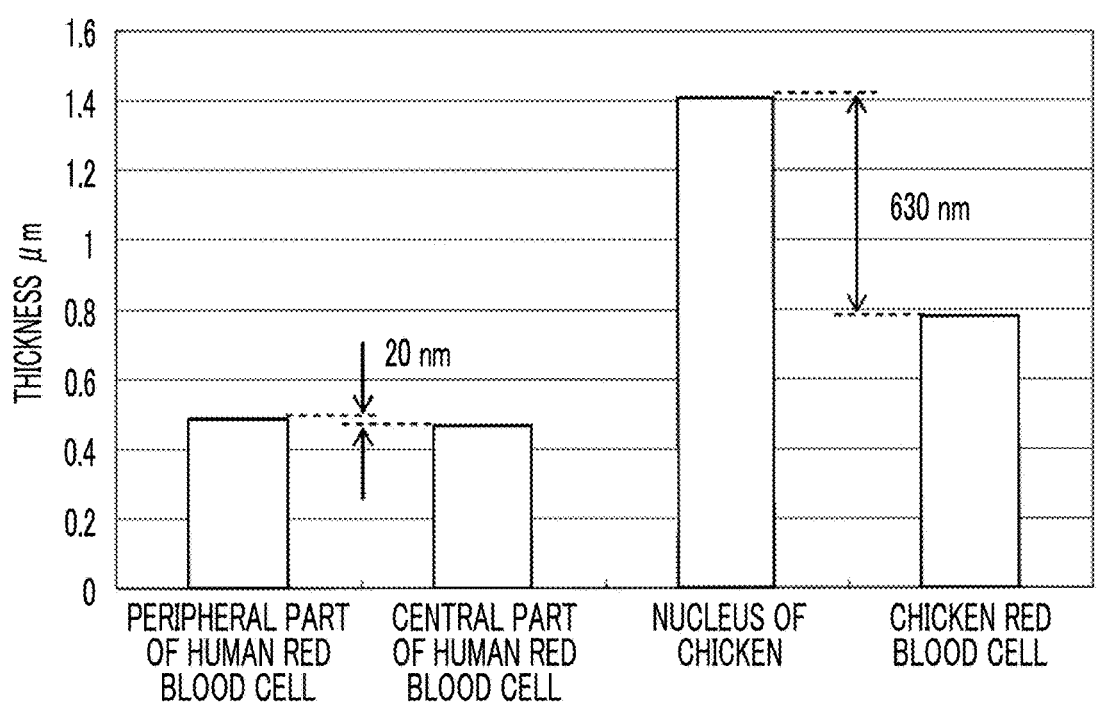
FIG. 11 is a graph showing a result obtained by observing a human red blood cell and a chicken red blood cell with a confocal microscope.

FIG. 11 is a graph showing a result obtained by observing a human red blood cell and a chicken red blood cell with a confocal microscope. The horizontal axis shows the object to be observed, and the vertical axis shows a thickness of the object to be observed. As shown in FIG. 11, in a case where the thickness of the peripheral part of the human non-nucleated red blood cell is approximately 0.49 μm (490 nm), the thickness of the central part is approximately 0.47 μm (470 nm). The difference in the thickness between the peripheral part and the central part of the human red blood cell is approximately 20 nm. On the other hand, the thickness of a nucleus of the chicken red blood cell (corresponding to the central part of the red blood cell) is approximately 1.41 μm (1410 nm), and the thickness of the chicken red blood cell (corresponding to the peripheral part) is approximately 0.78 μm (780 nm). The difference in the thickness between the peripheral part and the central part of the chicken red blood cell is approximately 630 nm.

An optical path difference L between light passing through the nucleus of the chicken and light that does not pass through the nucleus can be obtained by the expression $(1.36-1) \times \text{thickness}$. 1.36 is the refractive index of the cell, and 1 is the refractive index of the air. Since the thickness that is measured is 630 (nm), the optical path difference L is approximately 227 nm, according to the calculation.

On the other hand, according to the graph of the chicken red blood cell of FIG. 10A, in a case where the brightness ratios observed at 420 nm and the brightness ratios observed at 650 nm are compared, it is interpreted that the brightness ratios at these wavelengths tend to be roughly the same. That is, one cycle is estimated to be approximately 230 nm.

It is understood that the variation in the brightness ratios reflects the thickness of the nucleated red blood cell (optical path difference), from the optical path difference L (227 nm) obtained with the confocal microscope and one cycle (230 nm) of the brightness ratios obtained from the plurality of phase difference images.

Next, in the brightness ratio acquisition step (Step S4), wavelength interval between adjacent light rays is preferably 72 nm to 540 nm. As described above, a cyclical tendency is observed in the brightness ratios obtained from the plurality of phase difference images. Thus, in a case of acquiring the plurality of phase difference images, it is preferable that the interval between wavelengths of at least two light rays are within this cycle. This cycle is related to a thickness of a nucleus (optical path difference L). The thickness of a nucleus is in the range of 0.2 μm to 1.5 μm. In a case of calculating using $(1.36-1) \times \text{thickness}$, which is an expression for obtaining the optical path difference L, the optical path difference L is 72 nm to 540 nm. The lower limit value is preferably 72 nm, more preferably 115 nm, and even more preferably 230 nm.

Specifically, the target cell sorting portion 58 of the control unit 50 sorts the target cells and the non-target cells from the plurality of target cell candidates, based on the brightness ratios acquired from the plurality of target cell candidates. The brightness ratios include the information which allows the target cell and the non-target cell to be distinguished.

In the present embodiment, using the red blood cell which is the target cell candidate, information regarding the thickness can be acquired from the brightness ratios, that is information regarding the presence or absence of a nucleus is acquired. In addition, the nucleated red blood cell which is the target cell and the non-nucleated red blood cell which is the non-target cell are sorted.

As described above, in the present embodiment, in a case where the target cells and the non-target cells are sorted from the target cell candidates, the target cell can be identified with high throughput, since the optical path difference is not measured. In addition, since the target cell candidates are selected based on the difference in the absorption coefficient with respect to the plurality of light rays having different wavelengths, and the brightness ratios between the central part and the peripheral part of each target cell candidate are acquired based on the plurality of phase difference images, robust selections, sorting, and identification of the target cell are possible.

In addition, in a case where the target cells included in the specimen are not placed on the reference plane, for example, even in a case where the surface on which the sample is smeared is not even, the target cells can be identified.

The method for identifying a target cell of the present embodiment will be described by exemplifying a case where a specimen is maternal blood, a target cell candidate is a red blood cell, a target cell is a nucleated red blood cell, and a non-target cell is a non-nucleated red blood cell. However, the present invention is not limited to this embodiment, and in general, the present invention can be applied to blood such as peripheral blood, and can be applied to the amniotic fluid of a pregnant woman, umbilical blood, and the like.

As the method for identifying a target cell of the present embodiment, a case where the method includes the specimen preparation step (Step S1), the image acquisition step (Step S2), the selection step (Step S3), the brightness ratio acquisition step (Step S4), and the sorting step (Step S5) has been described. However, as a preferred embodiment of the present invention, it is also possible to identify a target cell from a specimen that has been stored by being smeared on a slide glass in advance, instead of going through the specimen preparation step (Step S1).

Next, it is preferable that, in the present embodiment, the following acquisition step and analysis step are performed.

<Acquisition Step>

In an acquisition step, the target cells identified in the method for identifying a target cell of the present embodiment are isolated and collected. For example, in a case where the identified target cells are nucleated red blood cells, a known method can be used as a method for isolating and collecting the target cells, and in particular, a micromanipulation (MM) method or a laser microdissection (LMD) method is preferably used.

As a micromanipulation system, for example, various micromanipulators manufactured by NARISHIGE Group. can be combined. As a laser microdissection system, for example, a commercially available system such as a laser microdis section system PALM MicroBeam manufactured by ZEISS can be used.

<Analysis Step>

In an analysis step, genetic analysis is performed on the target cells isolated and collected in the acquisition step. In a case where the target cells are nucleated red blood cells, the analysis step includes an amplification step of amplifying a nucleic acid included in the chromosomes of the nucleated red blood cells, a definition step of defining the amounts of the amplified products of the nucleated red blood cells that have been amplified and confirming that the nucleated red blood cells are fetus-derived nucleated red blood cells through genetic analysis, and a determination step of determining the presence or absence of a numerical aberration in the fetus-derived chromosomes by comparing the amounts of the amplified products of DNA of the fetus-derived nucleated red blood cells.

[Amplification Step]

The amplification step is a step of amplifying a nucleic acid included in the chromosomes of the identified nucleated red blood cells or at least of the fetus-derived nucleated red blood cells. In the amplification step, DNA is extracted from cells isolated from a microwell plate or a smear preparation, and genome amplification is performed. The genome amplification can be performed using a commercially available kit.

In a genome amplification method used in the present embodiment, genomic DNA obtained by elution from the acquired cells through cell lysis using a surfactant and a proteolysis process using protease K or the like, which is a general method, is used.

As a whole genome amplification reagent, a reagent based on polymerase chain reaction (PCR) such as PicoPLEX WGA kit (New England Biolabs.), GenomePlex Single Cell Whole Genome Amplification kit (Sigma-Aldrich, Inc.), and a multiple annealing and looping-based amplification cycles (MALBAC) method (published in WO2012/166425A2) can be used. A reagent based on a strand displacement DNA synthesis reaction such as GenomiPhi (GE Healthcare) and REPLI-g (Qiagen) can also be used in the same way. In the present embodiment, it is preferable to use PicoPLEX WGA kit (New England Biolabs.).

Regarding the amplified product of DNA obtained through whole genome amplification, whether the DNA has been amplified or not can be confirmed by agarose gel electrophoresis or the like. In addition, it is preferable that the whole genome amplified product is purified using QIAquick PCR Purification Kit (QIAGEN).

The concentration of the amplified product of DNA obtained through the whole genome amplification can be measured using NanoDrop (Thermo Fisher Scientific Inc.), Quantus Fluorometer (Promega Corporation), BioAnalyzer (Agilent Technologies), or TapeStation (Agilent Technologies).

[Definition Step]

In the definition step, the amounts of the amplified products of the nucleated red blood cells amplified in the amplification step are defined, and fetus-derived nucleated red blood cells are confirmed from the nucleated red blood cells through genetic analysis.

[Genetic Analysis]

In the genetic analysis, DNA microarray, digital PCR, a next generation sequencer, and nCounter System (NanoString Technologies, Inc.) can be used, and in the present embodiment, from the viewpoint of accuracy and speed in analysis and from the viewpoint that a large number of samples can be processed at a time, it is preferable to use the next generation sequencer.

The next generation sequencer in the present embodiment refers to a sequencer classified by comparing with a capillary sequencer using the Sanger method (referred to as a first-generation sequencer). The next generation sequencer includes the second-generation, the third-generation, and the fourth-generation sequencers and sequencers that will be developed in the future. The most widely used next generation sequencer at the present moment is a sequencer using the principle of determining a base sequence by comprehending fluorescence or luminescence coupled with complementary strand synthesis using a DNA polymerase or complementary strand bonding by DNA ligase. Specifically, examples of the sequencer include MiSeq (Illumina, Inc.), HiSeq 2000 (Illumina, Inc.; HiSeq is a registered trademark), Roche 454 (F. Hoffmann-La Roche Ltd), and the like.

In a case where the amplified product of DNA obtained in the amplification step is analyzed with a next generation sequencer, a whole genome sequence, an exome sequence, and an amplicon sequence can be used.

Examples of means for alignment of sequence data obtained by the next generation sequencer include Burrows-Wheeler Aligner (BWA), and the sequence data is preferably mapped on the human genome sequence which is already known using BWA. Examples of means for analyzing a gene include SAMtools and BEDtools, and genetic polymorphism, genetic mutation, and the number of chromosomes are preferably analyzed by these analysis means.

<<<Analysis Using Allele>>>

After performing the whole genome amplification through the amplification step, it is possible to confirm that the nucleated red blood cells are fetus-derived nucleated red blood cells by determining a sequence of an allele.

The amount of the amplified product of DNA which is DNA amplified through the polymerase chain reaction (amplification step) and has a sequence of a region of 100 to 150 base pairs (bp) determined in advance in the chromosome that is an object to be checked for a numerical aberration in the target cell identified as a nucleated red blood cell is obtained using a sequencer. In the present embodiment, the chromosome which is an object to be checked is preferably chromosome 13. A fetus-derived nucleated red blood cell normally inherits one set of chromosomes from the father and the mother and has two copies of each chromosome, except for sex chromosomes. It is possible to sort the nucleated red blood cells into fetus-derived nucleated red blood cells or maternally derived nucleated red blood cells by analyzing the alleles of these sets of chromosomes and confirming the presence of a paternally derived gene.

Regarding the confirmation of the existence of a paternally derived gene, in a case where genetic analysis is simultaneously performed on a maternally derived cell, and an allele that does not exist in a maternally derived cell is present, the allele can be defined to be a paternally derived gene. In a case where a paternally derived gene is confirmed to be present, the nucleated red blood cell can be sorted as a fetus-derived nucleated red blood cell. The maternally derived cell which is subjected to genetic analysis is not particularly limited, but it is preferable to perform analysis of DNA from a white blood cell existing in the maternal blood.

In the case of analyzing an allele, it is preferable to analyze single nucleotide polymorphism (SNP (SNPs)), copy number polymorphism (CNP (CNPs)), or a short tandem repeat (STR).

As for the fetal gene, the fetus inherits a pair of genes from both parents, and genetic information is recorded by the sequence of chemical substances which are four kinds of bases. In the case of human, approximately 3 billion bases exist, and at a proportion of one out of 1000 to 2000 bases, a sequence portion that varies from person to person exists, and this is referred to as single nucleotide polymorphism. In a case where analysis is performed regarding this single nucleotide polymorphism, and a sequence of single nucleotide polymorphism can be identified in the nucleated red blood cell by comparing the nucleated red blood cell with a white blood cell which is a maternally derived cell, it is possible to confirm that the nucleated red blood cell is a fetus-derived nucleated red blood cell.

The copy number polymorphism and a short tandem repeat are regions in which a unit of a certain DNA sequence in DNA repeats and lines up in series. The copy number polymorphism and a short tandem repeat refer to these repeating regions. Since the fetus inherits copy number polymorphism and a short tandem repeat from the father and the mother, it is possible to confirm that a nucleated red blood cell having copy number polymorphism and a short tandem repeat that are different from the maternally derived white blood cell is a fetus-derived nucleated red blood cell.

<<Analysis Using Y Chromosome>>

In a case where the fetus is male, it is possible to confirm whether the nucleated red blood cell is a fetus-derived nucleated red blood cell by confirming the presence or absence of a Y chromosome after performing the whole genome amplification through the amplification step.

Since the Y chromosome only exists in a male, the Y chromosome is not present in a maternally derived nucleated red blood cell. Therefore, in a case where the fetus is male, it is possible to confirm that the nucleated red blood cell is a fetus-derived nucleated red blood cell, in a case where a Y chromosome can be confirmed to be present.

[Determination Step]

The determination step is a step of determining the presence or absence of a numerical aberration in the fetus-derived chromosomes by comparing the amounts of the amplified products of DNA of the fetus-derived nucleated red blood cells defined through the definition step.

As a standard (or a reference) for determining the presence or absence of a numerical aberration in the fetus-derived chromosomes, a chromosome other than the chromosome which is an object to be checked for a numerical aberration is selected, and the amplified amount of the amplified product of DNA having a sequence of a region of 100 to 150 bp determined in advance is obtained using a sequencer. The chromosome which becomes the standard (standard chromosome) is selected from an aspect of selecting at least one chromosome other than the chromosome which is the object to be checked for a numerical aberration in the chromosome of the fetus-derived nucleated red blood cell or an aspect of selecting a chromosome existing in a cell identified as a maternally derived nucleated red blood cell. In the present embodiment, it is preferable to select a chromosome existing in a cell identified as a maternally derived nucleated red blood cell.

Next, by using the ratio of the amount of the amplified product of DNA of the chromosome which is the object to be checked for a numerical aberration to the amount of the amplified product of DNA of the standard chromosome, the presence or absence of a numerical aberration in the fetus-derived chromosomes is determined. In a case where the fetus is in a normal state, the quantitative ratio between the amount of the amplified product of DNA of the fetus-derived chromosomes which is the object to be checked for a numerical aberration and the amount of the amplified product of DNA of the standard chromosome is expected to be nearly 1:1. In a case of a numerical aberration of a trisomy in which three copies of a chromosome exist instead of two copies of the chromosome as in normal cases, the ratio is expected to be 1.0:1.5 (or 2:3).

In addition, before the determination step, distribution of results of a ratio obtained multiple times of the amount of the amplified product of fetus-derived chromosomal DNA with respect to amounts of amplified products of DNA of maternally derived chromosomes in the case of being collected from the bodies of multiple pregnant mothers with normal fetuses and a distribution of results of a ratio obtained multiple times of the amount of amplified product of fetus-derived DNA with respect to an amount of an amplified product of maternally derived DNA of a mother pregnant with a fetus with a trisomy are obtained in advance. A cutoff value is set in a region where these two distributions do not overlap with each other, and by comparing the ratio of the amounts of the amplified products of DNA with this cutoff value, the presence or absence of a numerical aberration can be determined. In this case, the results of the checking for a numerical aberration can be interpreted as follows. In a case where the ratio of the amounts of the amplified products of DNA is equal to or lower than the cutoff value, the fetus is considered to be normal, and in a case where the ratio is equal to or greater than the cutoff value, the fetus is considered to have a numerical aberration of a trisomy.

EXPLANATION OF REFERENCES

10: target cell identification device
20: light source unit

22: light source
24: filter
30: imaging unit
32: ring stop
34: condenser lens
36: table
38: objective lens
40: phase plate
42: imaging device
50: control unit
52: image acquisition portion
54: target cell candidate selection portion
56: target cell brightness ratio acquisition portion
58: target cell sorting portion
100: personal computer
110: keyboard
120: display

What is claimed is:

1. A method for identifying a target cell, comprising:
an image acquisition step of irradiating a specimen with a plurality of light rays having different wavelengths and acquiring a plurality of phase difference images of the specimen;
a selection step of selecting a plurality of target cell candidates from the specimen based on a difference in absorption coefficients with respect to the plurality of light rays having different wavelengths;
a brightness ratio acquisition step of acquiring brightness ratios between a central part and a peripheral part of each target cell candidate based on the plurality of phase difference images; and
a sorting step of sorting a target cell and a non-target cell from the plurality of target cell candidates based on the brightness ratios.

2. The method for identifying a target cell according to claim 1, wherein the absorption coefficient is an absorption coefficient of cytoplasm.

3. The method for identifying a target cell according to claim 2,
wherein the absorption coefficient of cytoplasm is an absorption coefficient of hemoglobin.

4. The method for identifying a target cell according to claim 1,
wherein the wavelength of one light ray among the plurality of light rays having different wavelengths is 300 nm to 700 nm.

5. The method for identifying a target cell according to claim 1,
wherein information regarding thicknesses of the target cell and the non-target cell is obtained from the brightness ratios in the sorting step.

6. The method for identifying a target cell according to claim 1,
wherein the specimen is maternal blood,
the target cell candidate is a red blood cell,
the target cell is a nucleated red blood cell, and
the non-target cell is a non-nucleated red blood cell.

7. The method for identifying a target cell according to claim 1,
wherein the brightness ratio acquisition step further includes irradiating the plurality of target cell candidates with a light ray having a wavelength different from the different wavelengths of the plurality of light rays in the image acquisition step to acquire an additional phase difference image and acquiring a brightness ratio between a central part and a peripheral part of each target cell candidate based on the additional phase difference image.

8. The method for identifying a target cell according to claim 1,
wherein a wavelength interval between adjacent light rays in the plurality of light rays having different wavelengths is 72 nm to 540 nm.

9. A target cell identification device comprising:
a light source unit which emits a plurality of light rays having different wavelengths to a specimen;
an imaging unit which acquires a plurality of phase difference images of the specimen with respect to the plurality of light rays having different wavelengths; and
a control unit which identifies a target cell from the specimen based on the plurality of phase difference images,
wherein the control unit selects a plurality of target cell candidates from the specimen based on the difference in absorption coefficients with respect to the plurality of light rays having different wavelengths, acquires brightness ratios between a central part and a peripheral part of each target cell candidate based on the plurality of phase difference images, and sorts a target cell and a non-target cell from the plurality of target cell candidates based on the brightness ratios.

10. The target cell identification device according to claim 9,
wherein the control unit controls the imaging unit, acquires an additional phase difference image by irradiating the plurality of target cell candidates with a light ray having a wavelength different from the different wavelengths of the plurality of light rays, and acquires a brightness ratio between a central part and a peripheral part of each target cell candidate based on the additional phase difference image.

* * * * *